United States Patent
Arakawa

(10) Patent No.: US 6,252,932 B1
(45) Date of Patent: *Jun. 26, 2001

(54) METHOD AND APPARATUS FOR ACQUIRING IMAGE INFORMATION FOR ENERGY SUBTRACTION PROCESSING

(75) Inventor: Satoshi Arakawa, Kanagawa-ken (JP)

(73) Assignee: Fuji Photo Film Co., Ltd., Kanagawa-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/120,137

(22) Filed: Jul. 22, 1998

(30) Foreign Application Priority Data

Jul. 22, 1997 (JP) .................................... 9-195312

(51) Int. Cl.[7] ................................................... H05G 1/64
(52) U.S. Cl. .................... 378/98.9; 378/98.8; 378/98.11; 378/98.12
(58) Field of Search ................................ 378/98.8, 98.9, 378/98.11, 98.12

(56) References Cited

U.S. PATENT DOCUMENTS

| 3,894,181 | * | 7/1975 | Mistretta et al. ................. | 378/98.11 |
| 4,482,918 | * | 11/1984 | Keyes et al. ...................... | 378/98.11 |
| 4,541,106 | * | 9/1985 | Belanger et al. ................. | 378/98.11 |
| 4,792,900 | * | 12/1988 | Sones et al. ...................... | 600/407 |
| 4,887,604 | * | 12/1989 | Shefer et al. ..................... | 600/431 |
| 5,150,394 | * | 9/1992 | Karellas ............................ | 378/62 |
| 5,391,879 | * | 2/1995 | Tran et al. ........................ | 250/367 |
| 5,545,899 | * | 8/1996 | Tran et al. ........................ | 250/370.09 |
| 5,668,375 | * | 9/1997 | Petrick et al. .................... | 250/370.09 |
| 5,852,296 | * | 12/1998 | Tsukamoto et al. ............. | 250/370.09 |
| 5,877,501 | * | 3/1999 | Ivan et al. ........................ | 250/370.09 |
| 5,920,070 | * | 7/1999 | Petrick et al. .................... | 250/370.09 |

(List continued on next page.)

FOREIGN PATENT DOCUMENTS

| 59-211263 | 11/1984 | (JP) | ............................... H01L/27/14 |
| 1-216290 | 8/1989 | (JP) | .................................. G01T/1/24 |
| 2-164067 | 6/1995 | (JP) | ............................. H01L/27/146 |
| WO 92-06501 | 4/1992 | (WO) | ............................. H01L/27/14 |

OTHER PUBLICATIONS

"Signal, Noise, and Readout Considerations in the Development of Amorphous Silicon Photodiode Arrays for Radiotherapy and Diagnostic X–Ray Imaging"; Antonuk et al., SPIE vol. 1443 Medical Imaging V: Image Physics (1991) pp. 108–119.

(List continued on next page.)

*Primary Examiner*—Robert H. Kim
*Assistant Examiner*—Allen C. Ho
(74) *Attorney, Agent, or Firm*—Sughrue, Mion, Zinn, Macpeak & Seas, PLLC

(57) ABSTRACT

Radiation having a high energy level, in which high energy components have been emphasized relatively to other energy components, is irradiated to an object, and high energy image information corresponding to the radiation having a high energy level, which radiation carries image information of the object, is thereby stored on a radiation detector. The radiation detector is provided with a flat surface-like scintillator, which converts radiation into visible light, and a solid-state photodetector, which is overlaid upon the scintillator and is constituted of a plurality of solid-state photo detecting devices located in a matrix-like pattern. The stored high energy image information is read from the radiation detector. Thereafter, radiation having a low energy level, in which low energy components have been emphasized relatively to other energy components, is irradiated to the object, and low energy image information corresponding to the radiation having a low energy level, which radiation carries image information of the object, is thereby stored on the radiation detector. The stored low energy image information is read from the radiation detector.

6 Claims, 3 Drawing Sheets

U.S. PATENT DOCUMENTS 6,005,911 * 12/1999 Cheung .................................. 378/37
6,052,433 * 4/2000 Chao .................................. 378/98.9
6,072,855 * 6/2000 Arakawa ........................... 378/98.11

OTHER PUBLICATIONS

"Amorphous Silicon X–Ray Image Sensor", J. Chabbal et al., SPIE vol. 2708, pp. 499–510.

"Material Parameters in Thick Hydrogenated Amorphous Silicon Radiation Detectors", S. Qureshi et al.; Lawrence Berkely Laboratory, Universit of California; pp. 1–4.

"Metal/Amorphous Silicon Multilayer Radiation Detectors", Naruse et al., IEEE Transactions of Nuclear Science, vol. 36, No. 2, Apr. 1989, pp. 1347–1352.

* cited by examiner

METHOD AND APPARATUS FOR ACQUIRING IMAGE INFORMATION FOR ENERGY SUBTRACTION PROCESSING

BACKGROUND OF THE INVENTION

1. Field of the Invention

This invention relates to a method and apparatus for acquiring image information for energy subtraction processing. This invention particularly relates to a method and apparatus for acquiring image information for two-shot energy subtraction processing, in which two kinds of images are obtained with two times of exposure to radiation.

2. Description of the Prior Art

Techniques for reading out a recorded radiation image in order to obtain an image signal, carrying out appropriate image processing on the image signal, and then reproducing a visible image by use of the processed image signal have heretofore been known in various fields. Also, it has been proposed to use stimulable phosphors in radiation image recording and reproducing systems. Specifically, a radiation image of an object, such as a human body, is recorded on a sheet provided with a layer of the stimulable phosphor (hereinafter referred to as a stimulable phosphor sheet). The stimulable phosphor sheet, on which the radiation image has been stored, is then exposed to stimulating rays, such as a laser beam, which causes it to emit light in proportion to the amount of energy stored thereon during its exposure to the radiation. The light emitted by the stimulable phosphor sheet, upon stimulation thereof, is photoelectrically detected and converted into an electric image signal. The image signal is then processed and used for the reproduction of the radiation image of the object as a visible image on a recording material.

In the radiation image recording and reproducing systems wherein recording media, such as radiation film or stimulable phosphor sheets, are used, subtraction processing techniques for radiation images are often carried out on image signals detected from a plurality of radiation images of an object, which have been recorded on the recording media.

With the subtraction processing techniques for radiation images, an image is obtained which corresponds to a difference between a plurality of radiation images of an object recorded under different conditions. Specifically, a plurality of the radiation images recorded under different conditions are read out at predetermined sampling intervals, and a plurality of image signals thus detected are converted into digital image signals which represent the radiation images. The image signal components of the digital image signals, which components represent the image information recorded at corresponding sampling points (i.e., picture elements) in the radiation images, are then subtracted from each other. A difference signal is thereby obtained which represents the image of a specific structure or part of the object (hereinbelow also referred to as the pattern of a tissue, a structure, or the like) represented by the radiation images.

Basically, subtraction processing is carried out with either the so-called temporal (time difference) subtraction processing method or the so-called energy subtraction processing method. In the former method, in order for the image of a specific structure (for example, a blood vessel) of an object to be extracted from the image of the whole object, the image signal representing a radiation image obtained without injection of contrast media is subtracted from the image signal representing a radiation image in which the image of the specific structure (for example, a blood vessel) of the object is enhanced by the injection of contrast media. In the latter method, such characteristics are utilized that a specific structure of an object exhibits different levels of radiation absorptivity with respect to radiation with different energy distributions. Specifically, an object is exposed to several kinds of radiation with different energy distributions. Alternatively, the energy distribution of the radiation carrying image information of an object, is changed after it has been irradiated onto one of a plurality of radiation image recording media, after which the radiation impinges upon the second radiation image recording medium. In this manner, a plurality of radiation images are obtained in which different images of a specific structure are embedded. Thereafter, the image signals representing the plurality of the radiation images are weighted appropriately and subjected to a subtraction process in order to extract the image of the specific structure. The subtraction process is carried out with Formula (1) shown below.

$$S_{proc} = K_a \cdot H - K_b \cdot L + K_c \quad (1)$$

wherein Sproc represents the subtraction image signal obtained from the subtraction process, Ka and Kb represent the weight factors, Kc represents the bias component, H represents the image signal representing the radiation image recorded with the radiation having a high energy level, and L represents the image signal representing the radiation image recorded with the radiation having a low energy level. (The group of Ka, Kb, and Kc will be referred to as the parameters for the subtraction process.)

The energy subtraction processing may be classified into two kinds of methods. One of the methods is two-shot energy subtraction processing, and the other is one-shot energy subtraction processing.

With the two-shot energy subtraction processing, wherein the difference in energy level between the two shots can be kept large, the range of the subtraction image signal obtained from the subtraction process can be kept wide. Therefore, the contrast of the subtraction image reproduced from the subtraction image signal can be kept high.

In the two-shot energy subtraction processing, the two image signals to be subjected to the subtraction process should be obtained from the two times of exposure to radiation such that the image signal components of the two image signals may accurately represent corresponding picture elements in the two images. However, actually, it is not always possible to carry out the image recording operations successively and quickly for recording the two images with the two kinds of radiation having different energy distributions. Therefore, in cases where the object is a living body, particularly the chest, in which the motion of the heart, or the like, is violent, due to the interval of time occurring between the two times of exposure, it is not always possible to obtain the two images such that the corresponding picture elements in the two images may accurately coincide with each other. As a result, the signal-to-noise ratio of an energy subtraction image, which is obtained from the energy subtraction processing, cannot be kept high.

In the one-shot energy subtraction processing, two detectors are located one upon the other with an energy separating plate, or the like, intervening therebetween, and image signals are recorded respectively on the two detectors with a single, simultaneous exposure to radiation. Therefore, the image signals recorded on the two detectors can be obtained such that they may represent the images, in which the corresponding positions accurately coincide with each other. Also, since the energy separating plate, or the like, is located between the two detectors, the image signals recorded on the two detectors can be obtained with the radiation different in energy level. However, with the one-shot energy subtraction processing, the difference in energy level between the two detectors cannot be kept large, and the range of the subtraction image signal obtained from the subtraction process cannot be kept wide. Therefore, the contrast of the subtraction image reproduced from the subtraction image signal cannot be kept high.

As described above, the conventional one-shot energy subtraction processing and the conventional two-shot energy subtraction processing have their own drawbacks.

SUMMARY OF THE INVENTION

The primary object of the present invention is to provide a method of acquiring image information for energy subtraction processing, wherein two image signals to be subjected to a subtraction process are obtained such that they may represent images, which have been recorded with two kinds of radiation having a large difference in energy level and in which the corresponding positions coincide with each other with a practically sufficient accuracy.

Another object of the present invention is to provide an apparatus for carrying out the method of acquiring image information for energy subtraction processing.

In a method and apparatus for acquiring image information for energy subtraction processing in accordance with the present invention, a radiation detector is employed as a medium for storing the radiation image information. The radiation detector comprises a scintillator and a solid-state photodetector, which is overlaid upon the scintillator and is constituted of a plurality of solid-state photo detecting devices located in a matrix-like pattern. The radiation detector is firstly exposed to radiation having a high energy level, which radiation carries image information of an object, and high energy image information of the object is thereby stored on the radiation detector. Immediately after the exposure, a scan signal is given to the radiation detector, and the high energy image information is thereby read from the radiation detector (the charges retained in the respective solid-state photo detecting devices become erased). Also, immediately after the reading, the radiation detector is exposed to radiation having a low energy level, which radiation carries image information of the object, and low energy image information of the object is thereby stored in the radiation detector. In this manner, the time interval between the two shots is set to be as short as possible, and deviation in position between the high energy image information and the low energy image information is thereby restricted. Also, the high energy image information and the low energy image information are recorded by quickly changing the radiation having a high energy level and the radiation having a low energy level over to each other. The two pieces of image information for energy subtraction processing are thereby obtained with the two kinds of radiation having a sufficiently large difference in energy level.

Specifically, the present invention provides a method of acquiring image information for energy subtraction processing, wherein high energy image information of an object corresponding to radiation having a high energy level, in which high energy components have been emphasized relatively to other energy components, and low energy image information of the object corresponding to radiation having a low energy level, in which low energy components have been emphasized relatively to other energy components, are acquired, the method comprising the steps of:

i) irradiating the radiation having a high energy level to the object, the high energy image information corresponding to the radiation having a high energy level, which radiation carries image information of the object, being thereby stored on a radiation detector, the radiation detector being provided with a flat surface-like scintillator, which converts radiation into visible light, and a solid-state photodetector, which is overlaid upon the scintillator and is constituted of a plurality of solid-state photo detecting devices located in a matrix-like pattern, ii) reading the high energy image information, which has been stored on the radiation detector, iii) thereafter irradiating the radiation having a low energy level to the object, the low energy image information corresponding to the radiation having a low energy level, which radiation carries image information of the object, being thereby stored on the radiation detector, and iv) reading the low energy image information, which has been stored on the radiation detector.

Radiation detectors are described in, for example, Japanese Unexamined Patent Publication Nos. 59(1984)-211263 and 2(1990)-164067, PCT Patent Publication WO92/06501, "Signal, Noise, and Read Out Considerations in the Development of Amorphous Silicon Photodiode Arrays for Radiotherapy and Diagnostic X-ray Imaging," L. E. Antonuk et al., University of Michigan, R. A. Street Xerox, PARC, SPIE Vol. 1443, Medical Imaging V; Image Physics (1991), pp. 108–119, and "Amorphous Silicon X-ray Image Sensor," J. Chabbal, et al., SPIE, Vol. 2708, 1991, pp.499–510. The radiation detector comprises a solid-state photodetector and a scintillator, which is overlaid on the solid-state photodetector and converts radiation into visible light. The solid-state photodetector comprises a substrate, which may be constituted of, for example, quartz glass having a thickness of 3 mm, and a plurality of solid-state photo detecting devices, which are located in a matrix-like pattern on the substrate. Each of the solid-state photo detecting devices is constituted of a transparent conductive film, a conductive film, and an amorphous semiconductor film intervening therebetween. The solid-state photodetector also comprises a plurality of signal conductors and a plurality of scan conductors, which extend in a matrix-like pattern so as to intersect perpendicularly to each other.

The radiation detector is located such that the scintillator may stand facing the side from which radiation is incident. In this state, radiation carrying image information of an object is irradiated to the radiation detector. The radiation impinges directly upon the scintillator and is converted by the scintillator into visible light. The visible light is then detected by a photoelectric conversion means of each of the solid-state photo detecting devices and converted into an image signal, which represents the radiation image of the object. The image signal is read by a predetermined reading means from a transfer means of each of the solid-state photo detecting devices of the radiation detector.

The aforesaid operation for reading the image signal from the radiation detector can be carried out simply by giving the reading scan signal to the radiation detector. Therefore, the reading operation can be carried out markedly more quickly than with an image read-out operation in the conventional image information acquiring techniques, wherein X-ray film requiring the developing and fixing processes or the stimulable phosphor sheet requiring the stimulating-ray scanning and light guiding processes are employed as the recording medium. Specifically, the aforesaid operation for reading the image signal from the radiation detector can be carried out instantaneously. Therefore, even if a plurality of pieces of image information are recorded by successively carrying out the exposure to the radiation at time intervals of 50 milliseconds to 100 milliseconds, the recorded pieces of image information can be read successively in synchronization with the exposure to the radiation.

Also, as a result of the operation for reading the image information from the radiation detector, the charges having been accumulated in the solid-state photodetector are discharged. Therefore, simultaneously with the discharging, the image information having been stored on the radiation detector is erased automatically. Accordingly, it is not necessary to carry out an erasing operation besides the image read-out operation as in cases where the stimulable phosphor sheet is employed as the recording medium. With the radiation detector, the operations can thus be kept simple.

In the method of acquiring image information for energy subtraction processing in accordance with the present invention, one of radiation detectors, which is not provided with the scintillator as an essential constitution element, may also be employed, depending upon the constitution of the solid-state photodetector.

Examples of radiation detectors having no scintillator and directly detecting radiation include the following:

(i) A solid-state photodetector having a thickness approximately 10 times as large as the ordinary thickness, which thickness is taken in the direction along which radiation is transmitted. The solid-state photodetector is described in, for example, "Material Parameters in Thick Hydrogenated Amorphous Silicon Radiation Detectors," Lawrence Berkeley Laboratory, University of California, Berkeley, Calif. 94720 Xerox Parc. Palo Alto. Calif. 94304.

(ii) A solid-state photodetector comprising two or more layers overlaid via a metal plate with respect to the direction along which radiation is transmitted. The solid-state photodetector is described in, for example, "Metal/Amorphous Silicon Multilayer Radiation Detectors, IEE TRANSACTIONS ON NUCLEAR SCIENCE, Vol. 36, No. 2, April 1989.

(iii) A radiation detector comprising a semiconductor, such as CdTe. The radiation detector is proposed in, for example, Japanese Unexamined Patent Publication No. 1(1989)-216290.

With these radiation detectors, no scintillator is used, and radiation is directly detected and converted into an electric signal, or the like. As in the aforesaid radiation detector utilizing the scintillator, the radiation detectors utilizing no scintillator may also be employed in the method of acquiring image information for energy subtraction processing in accordance with the present invention.

In the method of acquiring image information for energy subtraction processing in accordance with the present invention, predetermined radiation may be employed as the radiation having a low energy level, and radiation, which is obtained by passing the predetermined radiation through a low energy component absorbing member having characteristics such that an absorptivity with respect to the low energy components may be higher than an absorptivity with respect to the high energy components, may be employed as the radiation having a high energy level. Alternatively, the radiation having a high energy level or the radiation having a low energy level may be radiated selectively out of a single radiation source, which is capable of radiating the radiation having a high energy level and the radiation having a low energy level such that they may be changed over to each other. In cases where the radiation having a high energy level is to be obtained by passing the predetermined radiation through the low energy component absorbing member, the low energy component absorbing member may be moved into and out of the position between the radiation source and the object. In this manner, the radiation having a high energy level and the radiation having a low energy level can be changed over to each other.

Further, the irradiation of the radiation having a low energy level should preferably be carried out within 100 milliseconds after the irradiation of the radiation having a high energy level. The irradiation of the radiation having a low energy level should more preferably be carried out within 50 milliseconds after the irradiation of the radiation having a high energy level.

The foregoing also apply to an apparatus in accordance with the present invention, which will be described below.

The present invention also provides an apparatus for acquiring image information for energy subtraction processing, wherein high energy image information of an object corresponding to radiation having a high energy level, in which high energy components have been emphasized relatively to other energy components, and low energy image information of the object corresponding to radiation having a low energy level, in which low energy components have been emphasized relatively to other energy components, are acquired, the apparatus comprising:

i) a radiation source, which is capable of radiating the radiation having a high energy level and the radiation having a low energy level such that they may be changed over to each other, ii) a radiation detector, which is located at a position that receives the radiation having been irradiated to the object and carrying image information of the object, the radiation detector being provided with a flat surface-like scintillator, which converts radiation into visible light, and a solid-state photodetector, which is overlaid upon the scintillator and is constituted of a plurality of solid-state photo detecting devices located in a matrix-like pattern, and iii) a control means, which controls operations for:
  a) radiating the radiation having a high energy level out of the radiation source, the high energy image information being thereby stored on the radiation detector,
  b) reading the high energy image information, which has been stored on the radiation detector,
  c) thereafter radiating the radiation having a low energy level out of the radiation source, the low energy image information being thereby stored on the radiation detector, and
  d) reading the low energy image information, which has been stored on the radiation detector.

In the apparatus for acquiring image information for energy subtraction processing in accordance with the present invention, the radiation source may be provided with:

a radiation tube for radiating a single kind of radiation, a low energy component absorbing member, which has characteristics such that an absorptivity with respect to the low energy components of the radiation may be higher than an absorptivity with respect to the high energy components of the radiation, the low energy component absorbing member being located such that it can be moved into a position between the radiation tube and the object and can be retracted from the position, and a drive means for moving the low energy component absorbing member into the position between the radiation tube and the object and retracting the low energy component absorbing member from the position in accordance with a predetermined instruction signal.

Alternatively, the radiation source may be constituted of a single radiation tube, which is capable of radiating the radiation having a high energy level and the radiation having a low energy level such that they may be changed over to each other in accordance with a predetermined instruction signal.

Also, the length of time occurring between the irradiation of the radiation having a high energy level and the irradiation of the radiation having a low energy level should preferably be set to be at most 100 milliseconds by the control means. The length of time occurring between the irradiation of the radiation having a high energy level and the irradiation of the radiation having a low energy level should more preferably be set to be at most 50 milliseconds.

With the method and apparatus for acquiring image information for energy subtraction processing in accordance with the present invention, the radiation detector, which is provided with the solid-state photodetector, is firstly exposed to the radiation having a high energy level, which radiation carries image information of the object, and the high energy image information of the object is thereby stored on the radiation detector. Immediately after the exposure, the high energy image information is read from the radiation detector. As a result of the reading, the charges having been accumulated in the radiation detector are discharged. During the period of the reading, the radiation, which is radiated out of the radiation source, is changed over from the radiation having a high energy level to the radiation having a low energy level. Also, immediately after the reading, the radiation detector is exposed to the radiation having a low energy level, which radiation carries image information of the object, and the low energy image information of the object is thereby stored on the radiation detector. The operations from the irradiation of the radiation having a high energy level to the irradiation of the radiation having a low energy level are carried out very quickly (for example, within 100 milliseconds). In this manner, the time interval between the two shots can be set to be as short as possible, and deviation in position between the high energy image information and the low energy image information can thereby be restricted. Also, the high energy image information and the low energy image information are recorded by quickly changing the radiation having a high energy level and the radiation having a low energy level over to each other. The two pieces of image information for energy subtraction processing can thereby be obtained with the two kinds of radiation having a sufficiently large difference in energy level.

Therefore, the occurrence of noise due to deviation in position between the two images subjected to the energy subtraction processing can be restricted. Also, the two images subjected to the energy subtraction processing can be formed with the two kinds of radiation having a large difference in energy level. Accordingly, an energy subtraction image, which has a high contrast and good image quality, can be obtained from the energy subtraction processing.

DESCRIPTION OF THE PREFERRED EMBODIMENTS

The present invention will hereinbelow be described in further detail with reference to the accompanying drawings.

Figure 1:
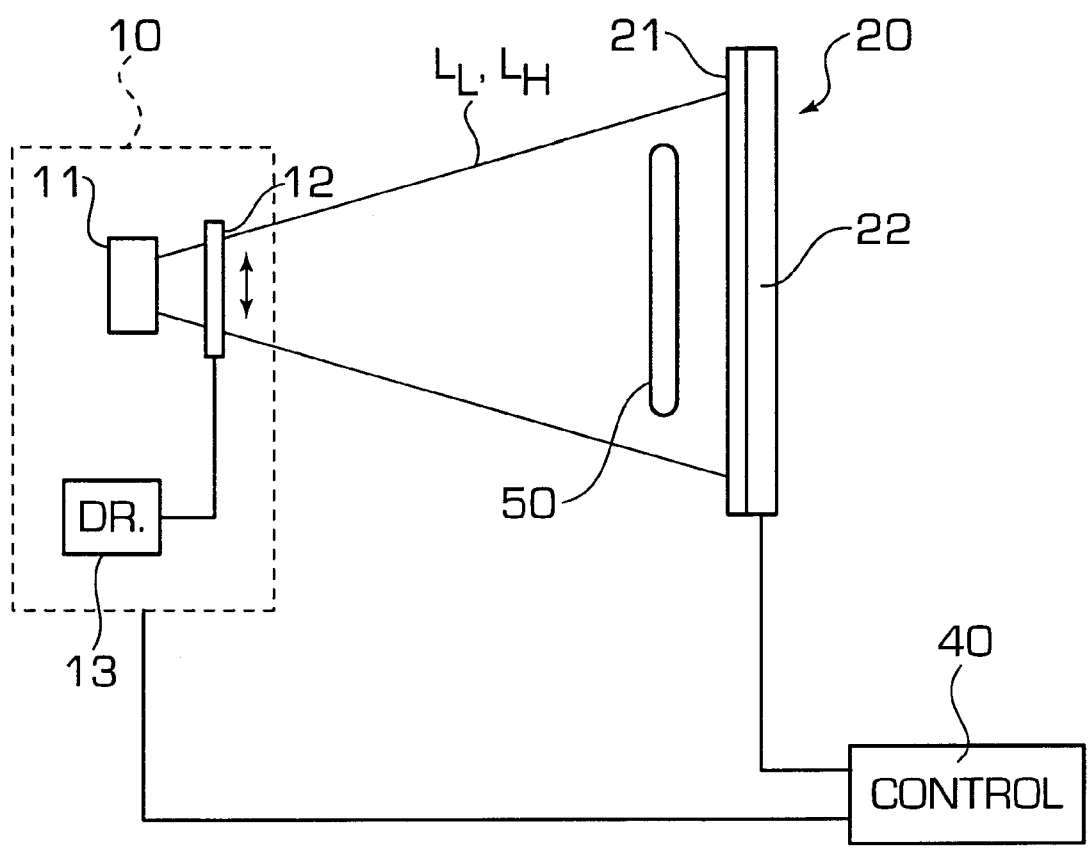
FIG. 1 is a schematic view showing an embodiment of the apparatus for acquiring image information for energy subtraction processing in accordance with the present invention.

FIG. 1 is a schematic view showing a radiation image recording apparatus, which is an embodiment of the apparatus for acquiring image information for energy subtraction processing in accordance with the present invention.

With reference to FIG. 1, in the apparatus for acquiring image information for energy subtraction processing, high energy image information $S_H$ of an object 50 corresponding to radiation $L_H$ having a high energy level, in which high energy components have been emphasized relatively to other energy components, and low energy image information $S_L$ of the object 50 corresponding to radiation $L_L$ having a low energy level, in which low energy components have been emphasized relatively to other energy components, are acquired. The apparatus for acquiring image information for energy subtraction processing comprises a radiation source 10, which is capable of radiating the radiation $L_H$ having a high energy level and the radiation $L_L$ having a low energy level such that they may be changed over to each other. The apparatus also comprises a radiation detector 20, which is located at a position that receives the radiation L', which has been irradiated to the object 50 and has passed through the object 50. The apparatus further comprises a control means 40. The control means 40 controls operations for: (a) radiating the radiation $L_H$ having a high energy level out of the radiation source 10, the high energy image information $S_H$ being thereby stored on the radiation detector 20, (b) thereafter immediately reading the high energy image information $S_H$ from the radiation detector 20, (c) immediately after the reading, radiating the radiation $L_L$ having a low energy level out of the radiation source 10, the low energy image information $S_L$ being thereby stored on the radiation detector 20, and (d) reading the low energy image information $S_L$ from the radiation detector 20.

Specifically, the radiation source 10 is provided with a radiation tube 11 for radiating a single kind of radiation $L_o$, a low energy component absorbing member 12, and a drive means 13. The low energy component absorbing member 12 has the characteristics such that the absorptivity with respect to the low energy components of the radiation $L_o$ may be higher than the absorptivity with respect to the high energy components of the radiation $L_o$. The low energy component absorbing member 12 is located such that it can be moved into the position between the radiation tube 11 and the object 50 and can be retracted from the position. The drive means 13 moves the low energy component absorbing member 12 into the position between the radiation tube 11 and the object 50 and retracting the low energy component absorbing member 12 from the position in accordance with a predetermined instruction signal.

In this embodiment, the tube voltage of the radiation tube 11 is 100 kv. Also, a Cu (copper) filter having a thickness of 1 mm is employed as the low energy component absorbing member 12.

The Cu filter 12 has a size such that the radiation (the radiation $L_H$ having a high energy level), which has passed through the Cu filter 12, may impinge upon the entire area of the radiation detector 20. Since the Cu filter 12 is located in the vicinity of the radiation tube 11, the size of the Cu filter 12 may be markedly smaller than the size of the radiation detector 20. Therefore, the distance, over which the Cu filter 12 must be moved when it is to be retracted from the position between the radiation tube 11 and the object 50, is short, and the movement of the Cu filter 12 can be finished within approximately 10 milliseconds.

The length of time occurring between the irradiation of the radiation $L_H$ having a high energy level and the irradiation of the radiation $L_L$ having a low energy level is set to be at most 100 milliseconds by the control means 40.

The radiation detector 20 will hereinbelow be described in detail. As illustrated in FIG. 1, the radiation detector 20 comprises a scintillator 21, which converts the incident radiation into visible light, and a solid-state photodetector 22, which detects the visible light having been generated by the scintillator 21 and photoelectrically converts the visible light into an image signal representing a radiation image of the object 50.

Figure 2:
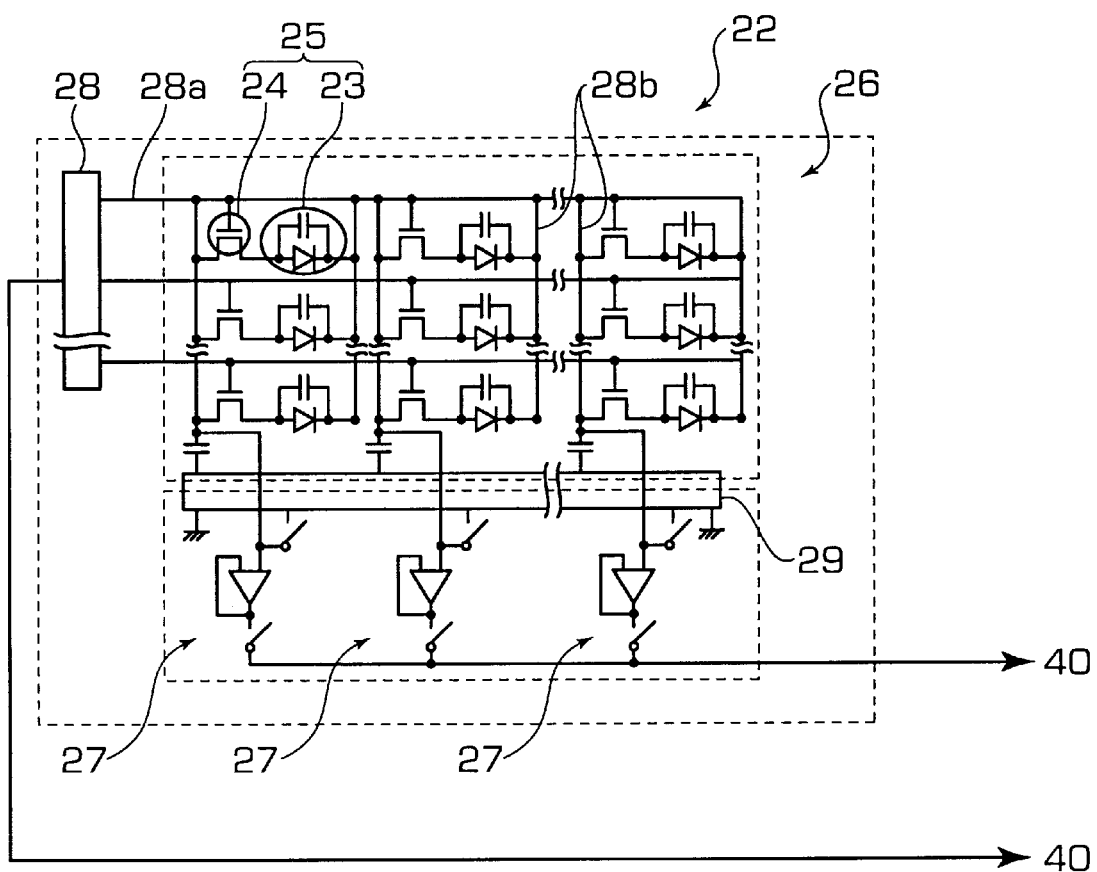
FIG. 2 is a schematic view showing a solid-state photodetector.

As illustrated in FIG. 2, the solid-state photodetector 22 comprises a solid-state photo detecting device group 26, which is constituted of a plurality of solid-state photo detecting devices 25, 25, . . . , which are arrayed in two-dimensional directions (i.e., in a matrix-like pattern). Each solid-state photo detecting device 25 is constituted of a photoelectric conversion means 23, which photoelectrically converts visible light into an analog image signal, and a transfer means 24, which temporarily stores the image signal generated by the photoelectric conversion means 23. The solid-state photodetector 22 also comprises a plurality of amplifiers 27, 27, . . . Each of the amplifiers 27, 27, . . . amplifies the image signal, which is fed out of the solid-state photo detecting devices 25, 25, . . . located along a single column of the array of the solid-state photo detecting devices 25, 25, . . . The solid-state photodetector 22 further comprises scan conductors 28a, 28a, . . . and signal conductors 28b, 28b, . . . The signal conductors 28b, 28b, . . . extend vertically in FIG. 2 and are connected to the solid-state photo detecting devices 25, 25, . . . and a multiplexer 29. The scan conductors 28a, 28a, . . . extend horizontally in FIG. 2 and are connected to the transfer means 24, 24, . . . of the solid-state photo detecting devices 25, 25, . . . and a scan pulse generator 28.

Output signals, which are obtained from the amplifiers 27, 27, . . . , are fed into the control means 40. A control signal, which is generated by the control means 40, is fed into the scan pulse generator 28.

Figure 3:
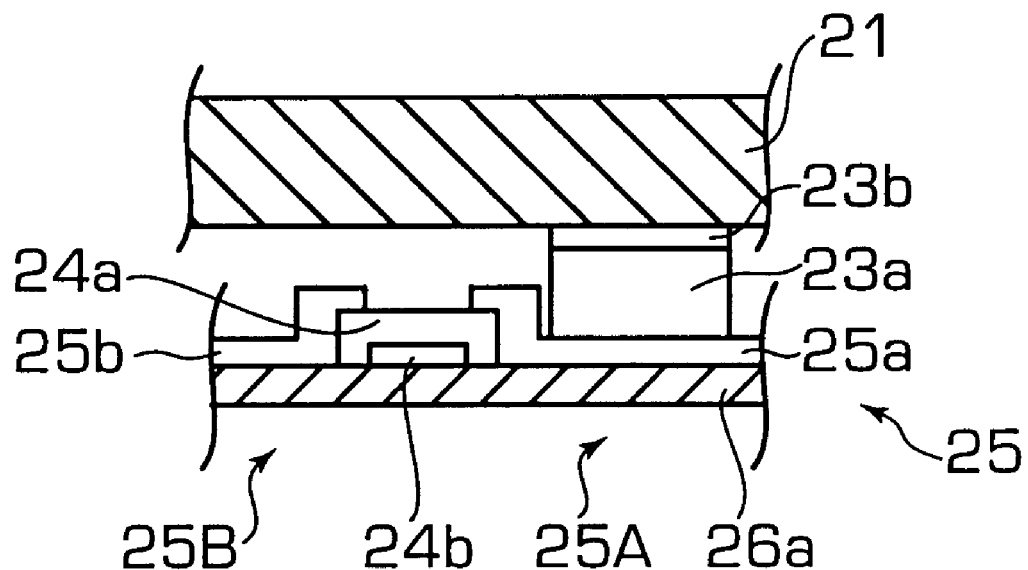
FIG. 3 is a sectional view showing a solid-state photo detecting device.

How each solid-state photo detecting device 25 is constructed will be described hereinbelow with reference to FIG. 3. As illustrated in FIG. 3, the solid-state photo detecting device 25 comprises a substrate 26a, which is constituted of a resin sheet, and signal conductors 25a and 25b, which are constituted of a conductive film overlaid with a pattern forming technique on the substrate 26a. The solid-state photo detecting device 25 also comprises a photodiode 25A, which is constituted of an amorphous silicon 23a and a transparent electrode 23b and which serves as the photoelectric conversion means 23. The solid-state photo detecting device 25 further comprises a thin-film transistor 25B, which is constituted of an amorphous silicon 24a and a transfer electrode (gate) 24b formed in the region inside of the amorphous silicon 24a and which serves as the transfer means 24.

The signal conductor 25b serves as a drain and is connected to the signal conductor 28b described above. The transfer electrode 24b is connected to the scan conductor 28a. The plurality of the solid-state photo detecting devices 25, 25, . . . having the structure described above are arrayed in two-dimensional directions, and the solid-state photo detecting device group 26 is thereby constituted. Also, the plurality of the solid-state photo detecting device groups 26, 26, . . . are arrayed, and the solid-state photodetector 22 is thereby obtained. The solid-state photodetector 22 is overlaid upon the scintillator 21, which may be constituted of a phosphor, such as $Gd_2O_2S$ or CsI. In this manner, the radiation detector 20 is obtained.

How this embodiment of the apparatus for acquiring image information for energy subtraction processing operates will be described hereinbelow.

Firstly, the radiation $L_o$ is produced by the radiation tube 11 at a tube voltage of 100 kv and is irradiated for a short time via the Cu filter 12 toward the object 50, which lies on the radiation detector 20. When the radiation $L_o$ passes through the Cu filter 12, the low energy components of the radiation are attenuated. As a result, the radiation $L_H$ having a high energy level, in which the high energy components have been emphasized relatively, is radiated out of the Cu filter 12. The radiation $L_H$ having a high energy level is irradiated to the object 50. The radiation $L_H$ having a high energy level, which has passed through the object 50, impinges upon the radiation detector 20.

The radiation $L_H$ having a high energy level, which impinges upon the radiation detector 20, firstly impinges upon the scintillator 21 and is converted thereby into visible light $LL_H$ (corresponding to the radiation $L_H$ having a high energy level). The visible light $LL_H$, which has thus been generated by the scintillator 21, is received by the photodiode 25A, which serves as the photoelectric conversion means 23 of each of the solid-state photo detecting devices 25, 25, . . . constituting the solid-state photodetector 22. As a result, signal charges $Q_H$ are generated in the photodiode 25A. In this manner, the signal charges $Q_H$ proportional to the luminance of the visible light, i.e. to the intensity of the incident radiation $L_H$, are generated in each of the solid-state photo detecting devices 25, 25, . . . As a result of the generation of the signal charges $Q_H$, the high energy image information SE is stored on the radiation detector 20.

Immediately after the aforesaid exposure has been carried out, specifically within approximately 10 milliseconds after the aforesaid exposure has been carried out, the drive means 13 retracts the Cu filter 12 from the position between the radiation tube 11 and the object 50 in accordance with the control operation of the control means 40.

Also, within approximately 30 milliseconds after the aforesaid exposure, the high energy image information $S_H$ is read from the radiation detector 20 in accordance with the control operation described below, which is carried out by the control means 40.

Specifically, a transfer pulse is fed from the scan pulse generator 28 to each of the solid-state photo detecting devices 25, 25, . . . , which are located along the top row in FIG. 2. As a result, the switch of the transfer means 24 of each of the solid-state photo detecting devices 25, 25, . . . , which are located along the top row in FIG. 2, is set to the on state. (In the on state, a voltage is applied across the transfer electrode 24b of each solid-state photo detecting device 25, and a current flows between the signal conductors 25a and 25b.) As a result, the signal charges, which have been generated in the photodiode 25A, are transferred through the thin-film transistor 25B, which serves as the transfer means 24. In this manner, the signal charges having been generated in the solid-state photo detecting devices 25, 25, ..., which are located along the top row in FIG. 2, are simultaneously fed into the multiplexer 29. The image signal components of the analog image signal (i.e. the image signal), which have been transferred from the respective solid-state photo detecting devices 25, 25, ..., are sequentially taken up from the multiplexer 29, amplified by the amplifiers 27, 27, ..., and then fed into the control means 40 as the image signal, which represents the high energy image information $S_H$ corresponding to the radiation $L_H$ having a high energy level. As a result of the reading of the image information from the radiation detector 20, the charges having been accumulated in the radiation detector 20 are discharged. Therefore, the reading and the erasing of the image information occur simultaneously.

As described above, the reading of the high energy image information $S_H$ is completed within approximately 30 milliseconds after the exposure. At the same time as the completion of the reading, in accordance with the control operation carried out by the control means 40, the radiation $L_o$ is produced by the radiation tube 11 at a tube voltage of 100 kv and is irradiated for a short time, without being passed through the Cu filter 12, toward the object 50, which lies on the radiation detector 20. Since the radiation $L_o$ does not pass through the Cu filter 12, the low energy components of the radiation are not attenuated as in the aforesaid first exposure. Therefore, the radiation $L_o$ serves as the radiation $L_L(=L_o)$ having a low energy level, in which the low energy components have been emphasized relatively. The radiation $L_L$ having a low energy level is irradiated to the object 50. The radiation LL having a low energy level, which has passed through the object 50, impinges upon the radiation detector 20.

As in the cases of the aforesaid radiation $L_H$ having a high energy level, the radiation $L_L$ having a low energy level, which impinges upon the radiation detector 20, firstly impinges upon the scintillator 21 and is converted thereby into visible light $LL_L$ (corresponding to the radiation $L_L$ having a low energy level). The visible light $LL_L$, which has thus been generated by the scintillator 21, is received by the photodiode 25A of each of the solid-state photo detecting devices 25, 25, .... As a result, signal charges $Q_L$ are generated in the photodiode 25A, and the low energy image information $S_L$ is thereby stored on the radiation detector 20.

Also, within approximately 30 milliseconds after the aforesaid exposure, the low energy image information $S_L$ is read from the radiation detector 20 in accordance with the control operation, which is carried out by the control means 40 in the same manner as that in the aforesaid high energy image information $S_H$. The low energy image information $S_L$ having thus been read is fed into the control means 40.

The aforesaid high energy image information $S_H$, which has firstly been fed into the control means 40, and the aforesaid low energy image information $S_L$, which has secondly been read from the radiation detector 20 and fed into the control means 40, are the pieces of image information, which have been formed with the different kinds of radiation having a larger difference in energy level than in the conventional one-shot energy subtraction processing and are suitable for the energy subtraction processing. Further, since the two pieces of image information can be acquired within a markedly short time (specifically, within as short as several tens of milliseconds) after the irradiation of the radiation having a high energy level, deviation in position between the image information represented by the image signals can be restricted more sufficiently than in the conventional two-shot energy subtraction processing.

As described above, with this embodiment of the apparatus for acquiring image information for energy subtraction processing in accordance with the present invention, the pieces of image information for energy subtraction processing, in which the deviation in position has been restricted to a higher extent than in the conventional two-shot energy subtraction processing and which have been formed with the different kinds of radiation having a larger difference in energy level than in the conventional one-shot energy subtraction processing, can be acquired. Therefore, from the thus acquired pieces of image information, an energy subtraction image can be obtained, in which the occurrence of noise due to deviation in position has been restricted more sufficiently than with the conventional techniques and which has a high contrast. Thus the energy subtraction image having good image quality can be obtained from the energy subtraction processing.

In the aforesaid embodiment, the radiation $L_H$ having a high energy level and the radiation $L_L$ having a low energy level are radiated out of the radiation source provided with the radiation tube for radiating a single kind of radiation, the low energy component absorbing member, and the drive means. The low energy component absorbing member has the characteristics such that the absorptivity with respect to the low energy components of the radiation may be higher than the absorptivity with respect to the high energy components of the radiation. The low energy component absorbing member is located such that it can be moved into the position between the radiation tube and the object and can be retracted from the position. The drive means moves the low energy component absorbing member into the position between the radiation tube and the object and retracting the low energy component absorbing member from the position in accordance with the predetermined instruction signal. However, the apparatus for acquiring image information for energy subtraction processing in accordance with the present invention is not limited to the embodiment, in which the aforesaid radiation source is employed. For example, the radiation source may be constituted of a single radiation tube, which is capable of radiating the radiation having a high energy level and the radiation having a low energy level such that they may be changed over to each other in accordance with a predetermined instruction signal received from the control means 40. As another alternative, a source for radiating only the radiation having a high energy level and a source for radiating only the radiation having a low energy level may be employed.

The low energy component absorbing member is not limited to the Cu filter, and one of other members may be employed. Also, as the radiation detector, a radiation detector having no scintillator may be employed.

What is claimed is:

1. A method of acquiring image information for energy subtraction processing, wherein high energy image information of an object corresponding to radiation having a high energy level, in which high energy components have been emphasized relatively to other energy components, and low energy image information of the object corresponding to radiation having a low energy level, in which low energy components have been emphasized relatively to other energy components, are acquired, the method comprising the steps of:

i) irradiating the radiation having a high energy level onto the object, the high energy image information corresponding to the radiation having a high energy level, which radiation carries image information of the object, being thereby stored on a radiation detector, said radiation detector being provided with a flat surface-like scintillator, which converts radiation into visible light, and a solid-state photodetector, which is overlaid upon and in direct contact with said scintillator and is constituted of a plurality of solid-state photo detecting devices located in a matrix-like pattern, ii) simultaneously reading the high energy image information which has been stored on said radiation detector, erasing the high energy image information from said radiation detector and preparing to irradiate the radiation having a low energy level, iii) thereafter irradiating the radiation having a low energy level onto the object, the low energy image information corresponding to the radiation having a low energy level, which radiation carries image information of the object, being thereby stored on said radiation detector, wherein the irradiation of said radiation having a low energy level is carried out within 100 milliseconds after the irradiation of said radiation having a high energy level, and iv) reading the low energy image information, which has been stored on said radiation detector.

2. A method as defined in claim 1 wherein predetermined radiation is employed as said radiation having a low energy level, and radiation, which is obtained by passing said predetermined radiation through a low energy component absorbing member having characteristics such that an absorptivity with respect to the low energy components is higher than an absorptivity with respect to the high energy components, is employed as said radiation having a high energy level.

3. A method as defined in claim 1 wherein said radiation having a high energy level and said radiation having a low energy level are radiated selectively out of a single radiation source, which radiates the radiation having a high energy level and the radiation having a low energy level such that they are changed over to each other.

4. An apparatus for acquiring image information for energy subtraction processing, wherein high energy image information of an object corresponding to radiation having a high energy level, in which high energy components have been emphasized relatively to other energy components, and low energy image information of the object corresponding to radiation having a low energy level, in which low energy components have been emphasized relatively to other energy components, are acquired, the apparatus comprising:

i) a radiation source, which selectively radiates the radiation having a high energy level and the radiation having a low energy level such that they are changed over to each other, ii) a radiation detector, which is located at a position that receives the radiation having been irradiated onto the object and carrying image information of the object, said radiation detector being provided with a flat surface-like scintillator, which converts radiation into visible light, and a solid-state photodetector, which is overlaid upon and in direct contact with said scintillator and is constituted of a plurality of solid-state photo detecting devices located in a matrix-like patter, and iii) a control means, which controls operations for:
   a) radiating the radiation having a high energy level out of said radiation source, the high energy image information being thereby stored on said radiation detector,
   b) simultaneously reading the high energy image information which has been stored on said radiation detector, erasing the high energy information from said radiation detector and preparing to irradiate the radiation having a low energy level,
   c) thereafter radiating the radiation having a low energy level out of said radiation source, the low energy image information being thereby stored on said radiation detector, wherein the length of time occurring between the radiating of the radiation having a high energy level and the radiating of said radiation having a low energy level is set to be at most 100 milliseconds by said control means, and
   d) reading the low energy image information, which has been stored on said radiation detector.

5. An apparatus as defined in claim 4 wherein said radiation source is provided with:

a radiation tube for radiating a single kind of radiation, a low energy component absorbing member, which has characteristics such that an absorptivity with respect to the low energy components is higher than an absorptivity with respect to the high energy components of said radiation, wherein said low energy component absorbing member is moved into a position between said radiation tube and the object and thereafter retracted from said position, and a drive means for moving said low energy component absorbing member into said position between said radiation tube and the object and retracting said low energy component absorbing member from said position in accordance with a predetermined instruction signal.

6. An apparatus as defined in claim 4 wherein said radiation source is constituted of a single radiation tube, which radiates the radiation having a high energy level and the radiation having a low energy level such that they are changed over to each other in accordance with a predetermined instruction signal.

* * * * *